United States Patent
Kroll

(10) Patent No.: US 7,103,412 B1
(45) Date of Patent: Sep. 5, 2006

(54) IMPLANTABLE CARDIAC STIMULATION DEVICE AND METHOD FOR DETECTING ASYMPTOMATIC DIABETES

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 532 days.

(21) Appl. No.: 10/429,133

(22) Filed: May 2, 2003

(51) Int. Cl.
*A61N 1/36* (2006.01)
(52) U.S. Cl. .......................................... 607/17; 607/9
(58) Field of Classification Search .................. 607/1, 607/9, 17, 18, 25; 600/300, 509, 510, 513, 600/516–517; 128/899
See application file for complete search history.

(56) References Cited

U.S. PATENT DOCUMENTS 5,741,211 A * 4/1998 Renirie et al. .............. 600/300
6,272,379 B1   8/2001 Fischell et al. ................ 607/5
6,572,542 B1 * 6/2003 Houben et al. ............. 600/300
6,650,931 B1 * 11/2003 McClure et al. ............ 600/510
6,695,790 B1 * 2/2004 Van Oort et al. ........... 600/508
6,813,514 B1 * 11/2004 Kroll et al. ................. 600/509
2004/0077962 A1 * 4/2004 Kroll .......................... 600/513
2004/0078065 A1 * 4/2004 Kroll .......................... 607/60

* cited by examiner

*Primary Examiner*—Robert E. Pezzuto
*Assistant Examiner*—Brian T. Gedeon

(57) ABSTRACT

An implantable cardiac stimulation device for determining whether a patient has asymptomatic diabetes. A pulse generator delivers pacing pulses to the heart. A sensing circuit senses internal cardiac signals. A processor is programmed to measure at least one characteristic of the cardiac signals, which are processed to determine whether the patient has asymptomatic diabetes. Relative changes in the measured characteristics over time are indicative of whether the patient has asymptomatic diabetes. The measured characteristics may include, alone or in combination, T-wave morphology, corrected QT internal, QT dispersion and signal averaged QRS width.

33 Claims, 5 Drawing Sheets

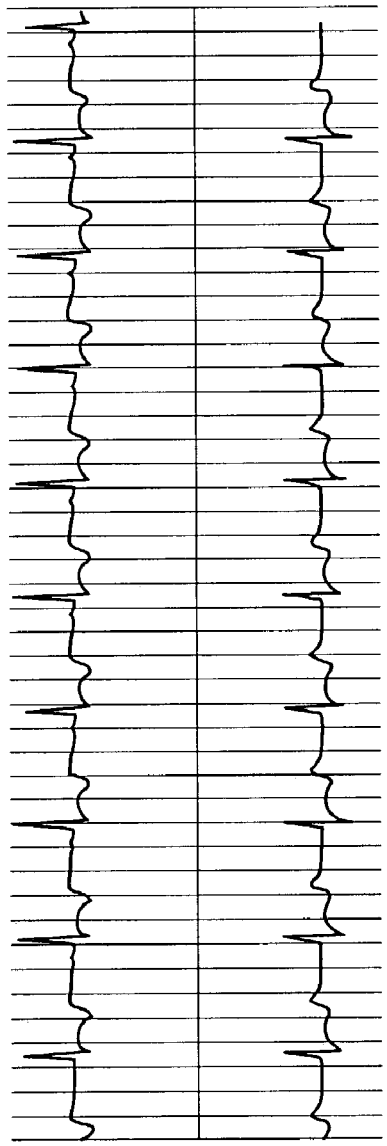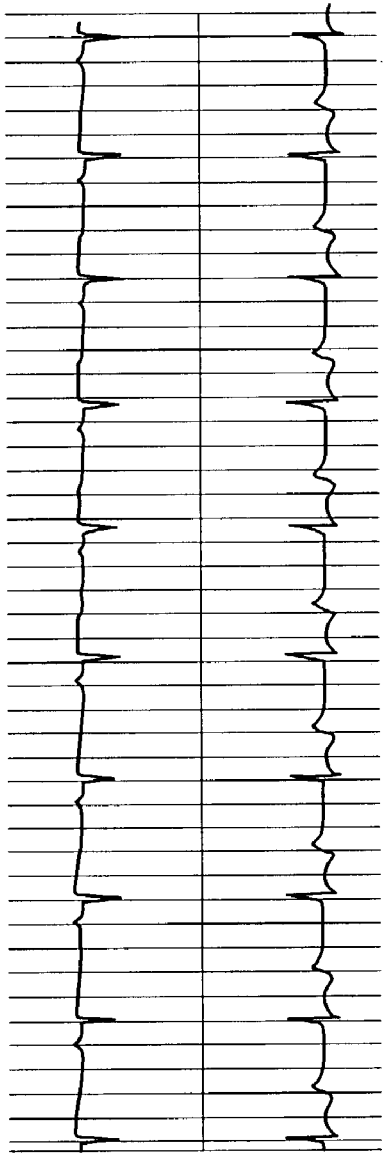
FIG. 5A
FIG. 5B

IMPLANTABLE CARDIAC STIMULATION DEVICE AND METHOD FOR DETECTING ASYMPTOMATIC DIABETES

FIELD OF THE INVENTION

The present invention relates in general to implantable cardiac devices, such as pacemakers, defibrillators, cardioverters, implantable cardioverter-defibrillators and similar implantable medical devices that are capable of monitoring and detecting electrical activities and events within the heart. In particular, this invention is directed to a system and a method for detecting asymptomatic diabetes based on abnormal cardiac signals that are associated with the onset of diabetes.

BACKGROUND OF THE INVENTION

Implantable cardiac devices ("ICDs") are well known in the art, and may operate to treat a variety of heart conditions. For example, included within the penumbra of ICDs are pacemakers, which may operate to maintain a healthy heart rate in a patient, or may operate to maintain a heart rate above a prescribed limit, such as, for example, to treat a bradycardia. Other examples of ICDs include cardioverter-defibrillators, which may operate to terminate potentially unhealthy arrhythmias or fibrillations. Some ICDs include both pacing circuitry and cardioverter-defibrillator circuitry. Other ICDs are designed to monitor a patient's heartbeat for diagnostic purposes.

Diabetes and heart disease share common risk factors, such as, for example, high blood pressure and cholesterol. Moreover, patients whose treatment for various heart conditions requires an ICD, are typically of an age group that is likely to develop diabetes during treatment with the ICD.

Abnormal cardiac rhythms, as measured by external electrocardiograms ("ECGs"), are known to be associated with diabetes. For example, T-wave oversensing in an ICD due to hyperglycemia has been reported. Specifically, it has been demonstrated that T-wave oversensing in the ICD was dependent on elevated serum glucose levels. Additionally, it has been reported that resting ECGs from young diabetics displayed prolonged corrected QT intervals.

Other studies have reported that ECGs showing flat or inverted T-waves were definitively associated with diabetes in otherwise healthy individuals. In fact, some reports suggest that there is an unusual prevalence of undetected diabetes among apparently healthy men who have non-specific T-wave abnormalities.

Even other studies have surmised that external ECGs could be used as an early marker for hypoglycemia because ECGs displayed a decrease in T-wave amplitude with declining blood glucose concentrations, while R-wave amplitudes remained unchanged. Accordingly, external ECGs facilitated observations that the R:T-wave ratio increased progressively in diabetic patients as blood glucose concentrations dipped to subnormal and hypoglycemic levels. It has been suggested that changes in external ECGs could be useful for detecting hypoglycemia and that a portable ECG recording system programmed with an algorithm capable of recognizing abnormal ECG patterns could alert a patient to check blood glucose levels if the measured R:T-wave ratio falls outside a pre-defined range.

Moreover, a system and method for monitoring diabetes-related blood constituents has been described. Specifically, the system provides a sensor that infers changes in blood glucose levels based upon external ECG signals and analyzes the external ECG signals to determine whether a group of parameters, including QRS, T-wave absolute mean, RMS values, QRS intervals, QT intervals, and RR intervals, is indicative of decreased blood glucose and/or insulin levels.

Accordingly, it would be advantageous to develop an ICD that, in addition to treating a particular heart condition, also is capable of continuously monitoring the patient's heartbeat for abnormal cardiac signals indicative of diabetes. Even more advantageous would be an ICD capable of monitoring at least one characteristic from internal cardiac signals, as opposed to monitoring external ECGs. Still more advantageous would be an ICD capable of monitoring multiple characteristics of the heartbeat to more accurately assess whether the patient has an abnormal heartbeat indicative of the early onset of diabetes and further capable of alerting the patient and physician of detected abnormalities as early as possible to increase the chances of effective diabetes treatment.

SUMMARY

What is described herein is a system and method for detecting asymptomatic diabetes based on abnormalities measured from internal cardiac signals (e.g. signals sensed from within the patient's body as opposed to signals sensed from outside of the patient). The system and method are adapted for use in an implantable cardiac stimulation device including a pulse generator that delivers atrial and ventricular pacing stimulation pulses to a heart. The system and method also include a sensing circuit that senses internal cardiac signals of the heart and circuitry connected to the pulse generator and the sensing circuit capable of measuring at least one characteristic of the internal cardiac signals and processes those characteristics to determine whether the patient has asymptomatic diabetes. In accordance with a broader aspect of the present invention, the system and method alert the patient when asymptomatic diabetes is detected.

One illustrative embodiment described herein provides a reconstructed external electrogram from the internal cardiac signals of the heart. In such an embodiment, at least one characteristic from the reconstructed external electrogram is measured and is used to determine whether the patient has asymptomatic diabetes. In another embodiment, the present invention provides a system and method wherein the sensing circuit senses internal cardiac signals of the heart by far-field electrocardiography.

Characteristics of internal cardiac signals that may be measured in the present invention include, but are not limited to, T-wave morphology, corrected QT interval, QT dispersion, and signal averaged QRS width. The present invention may be practiced by measuring any one of the above mentioned heartbeat characteristics alone or in any combination.

In yet another embodiment, a system and method are provided for detecting whether a patient has asymptomatic diabetes by measuring a T-wave morphology value, a corrected QT interval value, and a QT dispersion value, which combination of heartbeat characteristics are used to determine a diabetes mellitus indicator score. The diabetes mellitus indicator score is then compared to a threshold value. If the diabetes mellitus indicator score is greater than or equal to the threshold value for longer than a pre-determined period of time, the patient is alerted that asymptomatic diabetes has been detected.

BRIEF DESCRIPTION OF THE DRAWINGS

Further features and advantages of the present invention may be more readily understood by reference to the following description taken in conjunction with the accompanying drawings, in which:

FIG. 5A is an external ECG tracing (upper waveform), followed by an internal electrogram (lower waveform) from a patient; and FIG. 5B is an external ECG tracing (upper waveform), followed by an internal electrogram (lower waveform) from the same patient in FIG. 5A experiencing hyperglycemia.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
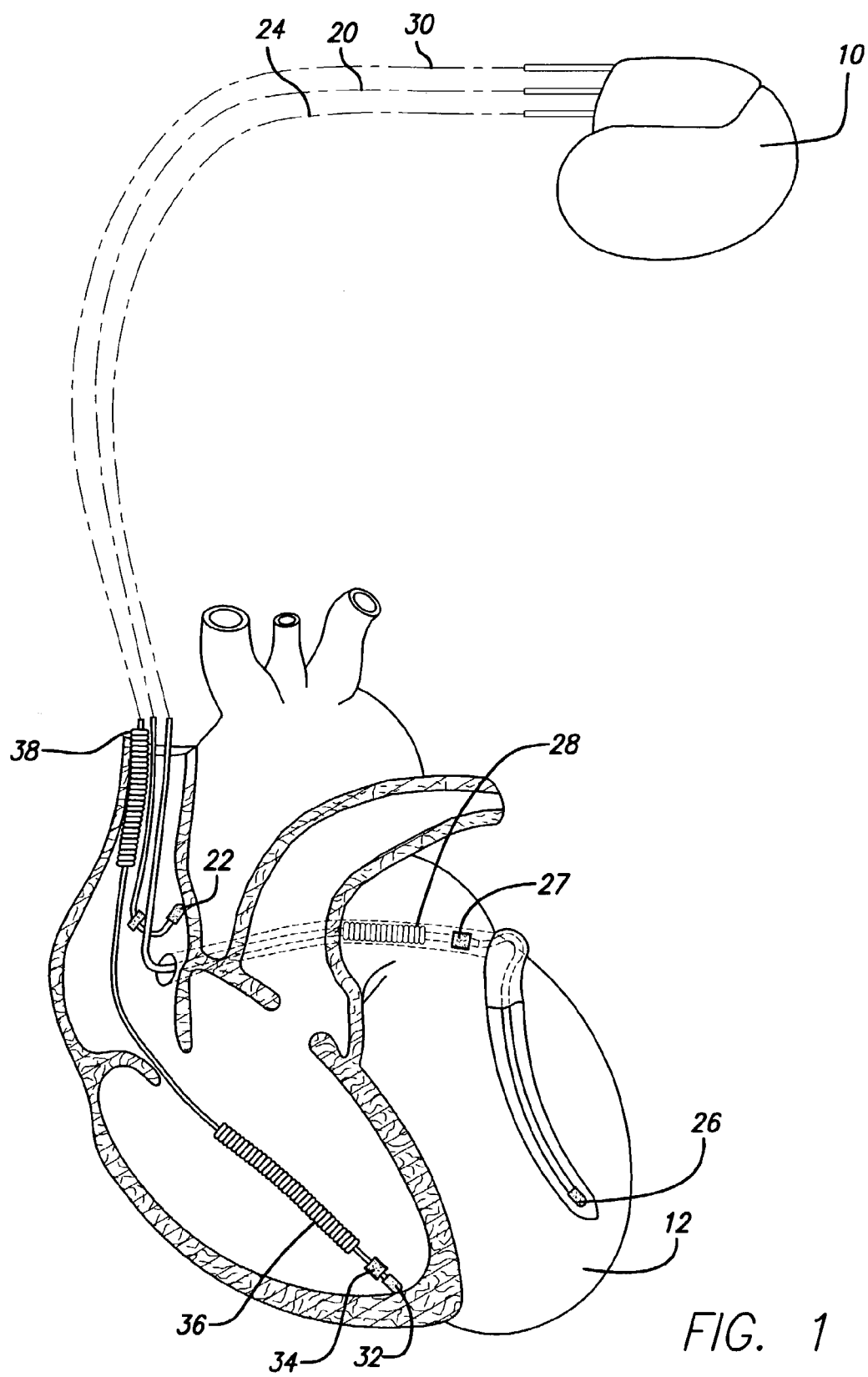
FIG. 1 is a simplified diagram illustrating an implantable medical device embodying the present invention in electrical communication with at least three leads implanted into a patient's heart for monitoring cardiac signals.

As shown in FIG. 1, there is a stimulation device 10 in electrical communication with a patient's heart 12 by way of three leads, 20, 24, and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to retrieve atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular ("RV") coil electrode 36, and a superior vena cava ("SVC") coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the SVC. Accordingly, the right ventricular lead 30 is capable of receiving cardiac signals and delivering stimulation in the form of pacing and shock therapy to the right ventricle.

Figure 2:
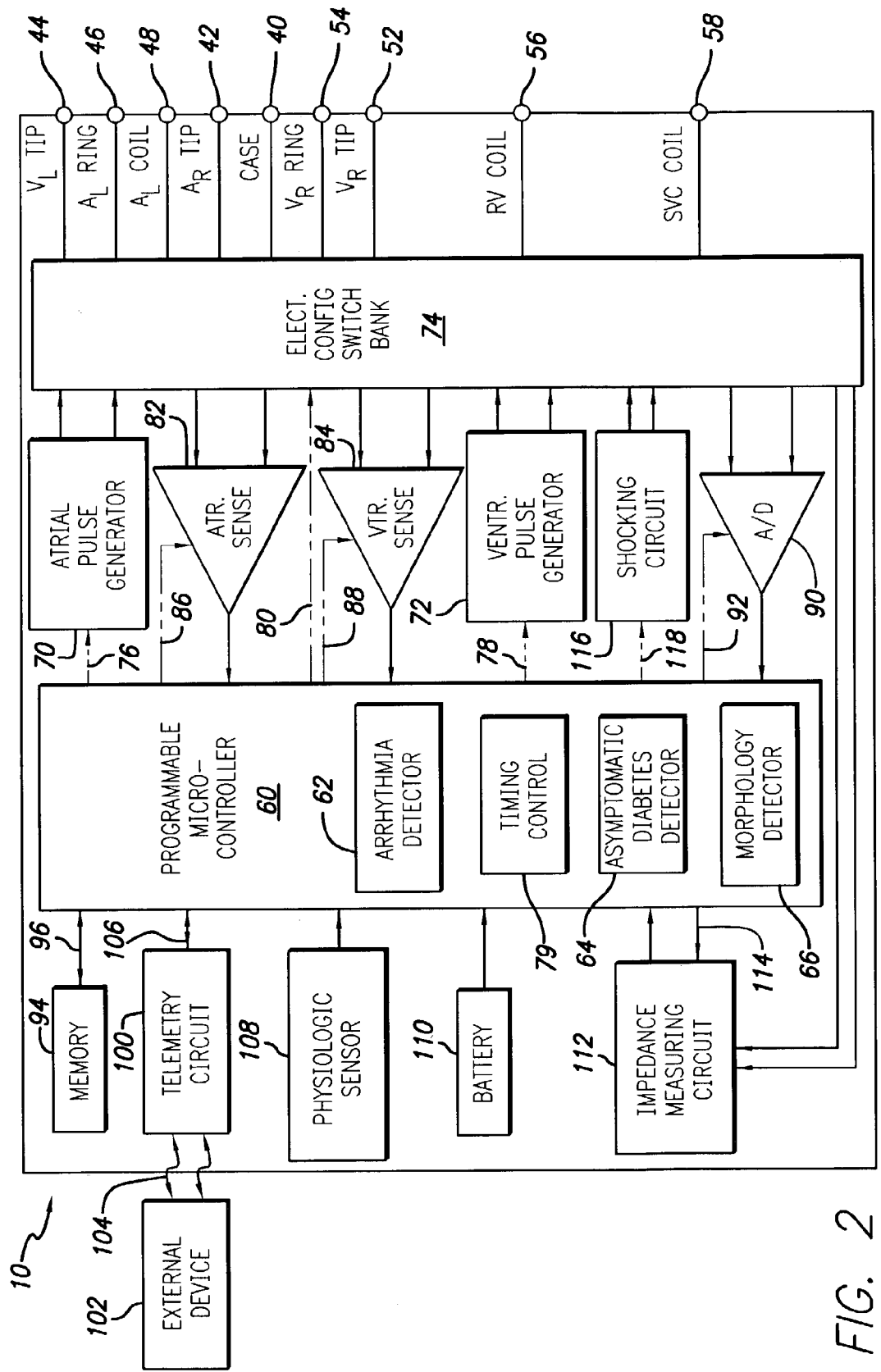
FIG. 2 is a functional block diagram of the device of FIG. 1 illustrating the basic elements for monitoring cardiac signals and analyzing whether the cardiac signals are indicative of asymptomatic diabetes.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of ordinary skill in the art could readily duplicate, eliminate or disable the appropriate circuitry in any desired combination to provide a device capable of treating the appropriate chamber(s) with cardioversion, defibrillation, and pacing stimulation.

The housing 40 for the stimulation device 10, shown schematically in FIG. 2, is often referred to as the "can," "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing, and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing, and shocking, the connector further includes a right ventricular tip terminal 52, a right ventricular ring terminal 54, a right ventricular shocking terminal 56, and a SVC shocking terminal 58, which are adapted for connection to the right ventricular tip electrode 32, right ventricular ring electrode 34, a RV coil electrode 36, and the SVC coil electrode 38, respectively.

In a preferred embodiment, the device senses internal cardiac signals by far-field electrocardiography. In another embodiment, the sensing and pacing leads (e.g. 32 and 34) are oriented in parallel to approximate far-field electrocardiography.

Traditionally, the term "far-field electrocardiography" is understood by those of ordinary skill in the implantable cardiac device art to refer to the undesirable sensing of distant cardiac signals to the exclusion or subordination of a local signal, such as, for example, sensing a signal in the atrium of an event that occurred in the ventricle, i.e., an R-wave. As used herein, the term "far-field electrocardiography" refers not only to the traditional definition described above, but also refers to the intentional gathering and sensing of signals generated both near and far. For example, as used herein, "far-field electrocardiography" refers to sensing signals from a large area of the heart by using large electrodes, which technique has been referred to by those of ordinary skill in the art as "global sensing."

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of the microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry, which is used to control the timing of such stimulation pulses (e.g., pacing rate atrio-ventricular (AV) delay, atrial interconduction (A—A) delay, pause durations or ventricular interconduction (V—V) delay, etc.) as well as to keep track of the timing of refractory periods, blanking periods, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 through the switch bank 74 for detecting the presence of cardiac activity in each of the four chambers of the heart. Accordingly, the atrial and ventricular sensing circuits, 82 and 84, may include dedicated sense amplifiers, multiplexed amplifiers or shared amplifiers. The switch bank 74 determines the "sensing polarity" of the cardiac signal by selectively closing the appropriate switches, as is known in the art. In this way, the clinician may program the sensing polarity independent of the stimulation polarity.

Each sensing circuit, 82 and 84, preferably employs one or more low power, precision amplifiers with programmable gain and/or automatic gain control, band pass filtering, and a threshold detection circuit, as is known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the controller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of the sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90, which is coupled to the microcontroller 60 via signal line 92. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60, or other detection circuitry, for detecting and measuring at least one characteristic of the internal cardiac signals from the heart 12 in response to an applied stimulus.

In accordance with this preferred embodiment, the data acquisition system 90 is coupled to the microcontroller 60 and senses internal cardiac signals from the heart 12 in responses to applied stimulation pulses. The internal cardiac signals generated by the data acquisition system 90 are stored in a memory 94 by the microcontroller 60 for processing by the microcontroller 60. More specifically, the microcontroller 60 isolates and measures at least one characteristic from each internal cardiac signal generated by the data acquisition system 90. Optionally, the internal cardiac signals may be used to reconstruct an external ECG, such as, for example, a 12 lead external ECG. Methods for reconstructing an external ECG from internal cardiac signals are known in the art.

The isolated and measured heartbeat characteristics, such as T-wave morphology, corrected QT interval, QT dispersion, and signal averaged QRS width, whether obtained directly from the internal cardiac signals or from the reconstructed electrogram, are quantified and stored in memory 94 prior to further analysis to determine whether the patient has asymptomatic diabetes. This process is repeated at regular intervals, as often as with every beat, or less often, as once or twice each day. The microcontroller 60 monitors timing events via timing control circuit 79. Over time, the stored, quantified measured values are used to determine whether the patient has asymptomatic diabetes, which determination may include calculation of a diabetes mellitus indicator score. Generally, relative changes in the isolated and measured heartbeat characteristics over time indicate that the patient has asymptomatic diabetes. Additionally, the device 10 may be programmed to perform a calibration step prior to sensing and measuring internal cardiac signals.

As may be noted in FIG. 2, the microcontroller 60 further includes a morphology detector 66. Morphology detection can be a very useful tool in detecting asymptomatic diabetes. Morphology detection is well known in the art and may be employed for discerning T-wave morphology, fully paced ventricular beats, intrinsic ventricular activation or ventricular fusion, atrial loss of capture, an atrial evoked response, or an atrial fusion beat. The morphology detector 66 may utilize the electrograms provided by the acquisition system 90.

For asymptomatic diabetes detection, the morphology detector 66 may be employed by the arrhythmia detector 62 to monitor T-wave morphology (i.e., T-wave oversensing, flat T-waves or inverted T-waves). Abnormal T-wave morphology is one characteristic indicative of asymptomatic diabetes. The microcontroller 60 further includes an asymptomatic diabetes detector 64, which typically contains algorithms useful for determining whether the isolated and measured heartbeat characteristics are indicative of asymptomatic diabetes. In one preferred embodiment, the asymptomatic diabetes detector 64 is programmed with the algorithms described in FIG. 3 and FIG. 4; however, one of ordinary skill in the art will appreciate that other algorithms may be used in the practice of the invention.

The microcontroller 60 is coupled to the memory 94 by a suitable data/address bus 96. In addition to internal cardiac signals, the memory 94 may store programmable operating parameters used or modified by the microcontroller 60, as required, in order to control the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, initial operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state or other physiologic stress of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV delay, V—V delay, etc.) at which the atrial and ventricular pulse generators, 70 and 72, generate stimulation pulses.

The stimulation device additionally includes a battery 110, which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 employs lithium/silver vanadium oxide batteries, as is true for most (if not all) such devices to date. The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 by a control signal 114. The impedance measuring circuit 112 has many known uses. However, it is not critical to the present invention and is therefore shown only for completeness.

If it is the primary function of the device 10 to function as an implantable cardioverter/defibrillator device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient), and/or synchronized with a R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
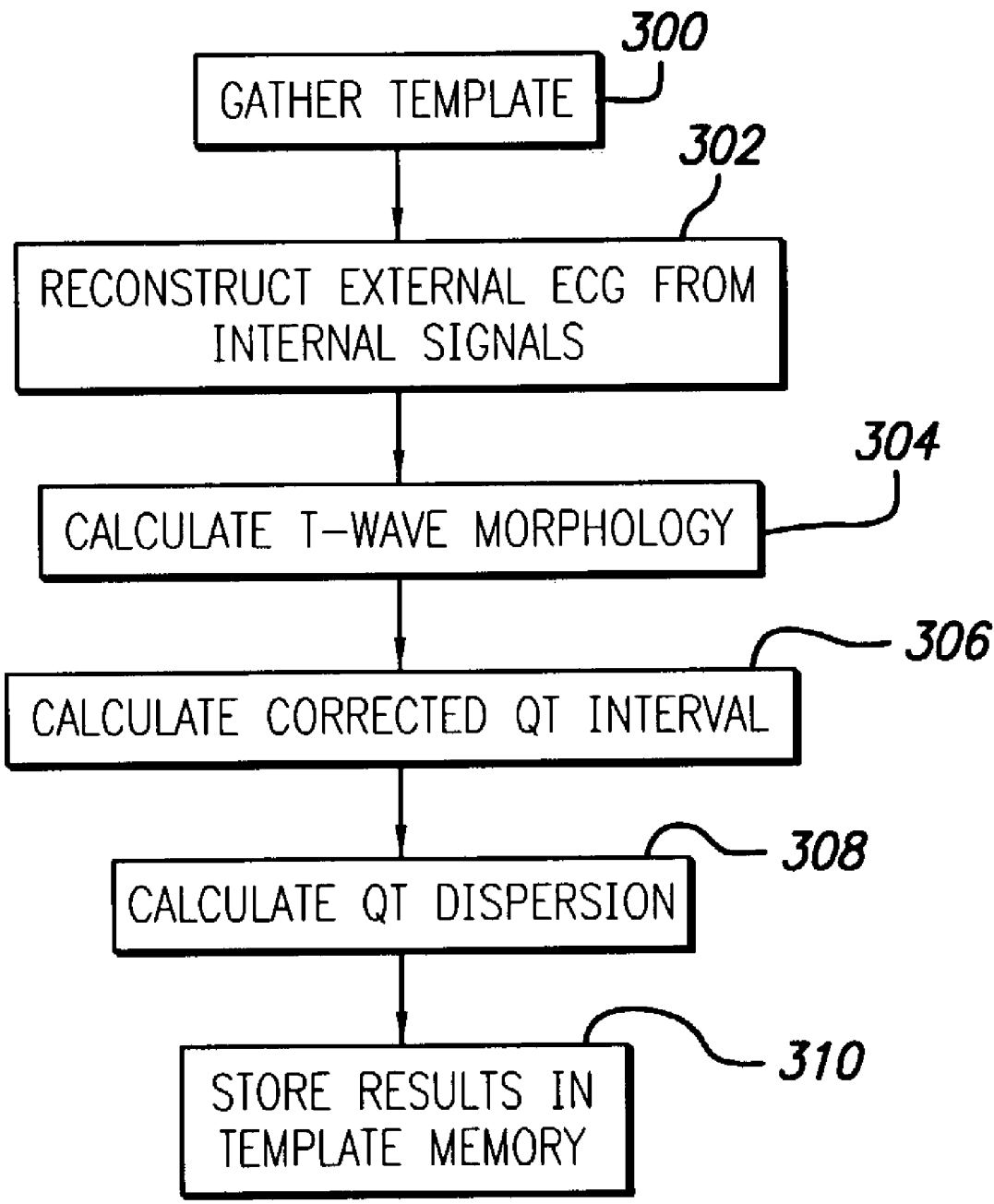
FIG. 3 is a flow chart describing an overview of a calibration algorithm of a preferred embodiment of the medical device of FIG. 1.

FIG. 3 shows a flow chart describing a calibration operation implemented in the device 10 in accordance with the preferred embodiment of the present invention. In this flow chart, the various algorithmic steps are summarized in individual "blocks." Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Specifically, FIG. 3 shows the preferred steps used to calibrate the device 10, either prior to implantation in the patient, or at a follow-up after the device 10 has been implanted. It is intended that the calibration operation will be implemented after it has been determined that the patient is not diabetic. Such determination may be made according to any method known to those skilled in the art, such as, for example, by a simple measure of the patient's glucose and/or insulin levels.

The calibration procedure begins with an activity block 300 wherein the device 10 is caused to gather a template. After the template is gathered, the calibration process progresses to the next block 302 wherein an external electrogram is reconstructed from the internal cardiac signals. The reconstructed external electrogram forms the basis for calculating a reference T-wave morphology value as the calibration process advances to activity block 304. Next, a reference corrected QT interval value is calculated as the calibration process advances to activity block 306. A reference QT dispersion value is calculated in activity block 308, and finally, in activity block 310, the reference T-wave morphology value, reference corrected QT interval value, and reference QT dispersion values are stored in memory 94 of the device 10 for subsequent use in determining a diabetes mellitus indicator score. In a more preferred embodiment, a 12 lead ECG is reconstructed from the internal cardiac signals. However, although FIG. 3 indicates that an external electrogram is reconstructed from the internal cardiac signals, such reconstruction of an external electrogram is not required in the practice of the present invention. In situations wherein the external electrogram is not reconstructed from internal cardiac signals, the data used to determine whether the patient has asymptomatic diabetes is gleaned directly from the internal cardiac signals.

In another embodiment, the calibration procedure also calculates a reference signal averaged QRS width value, which is also stored in memory 94 of the device 10.

Figure 4:
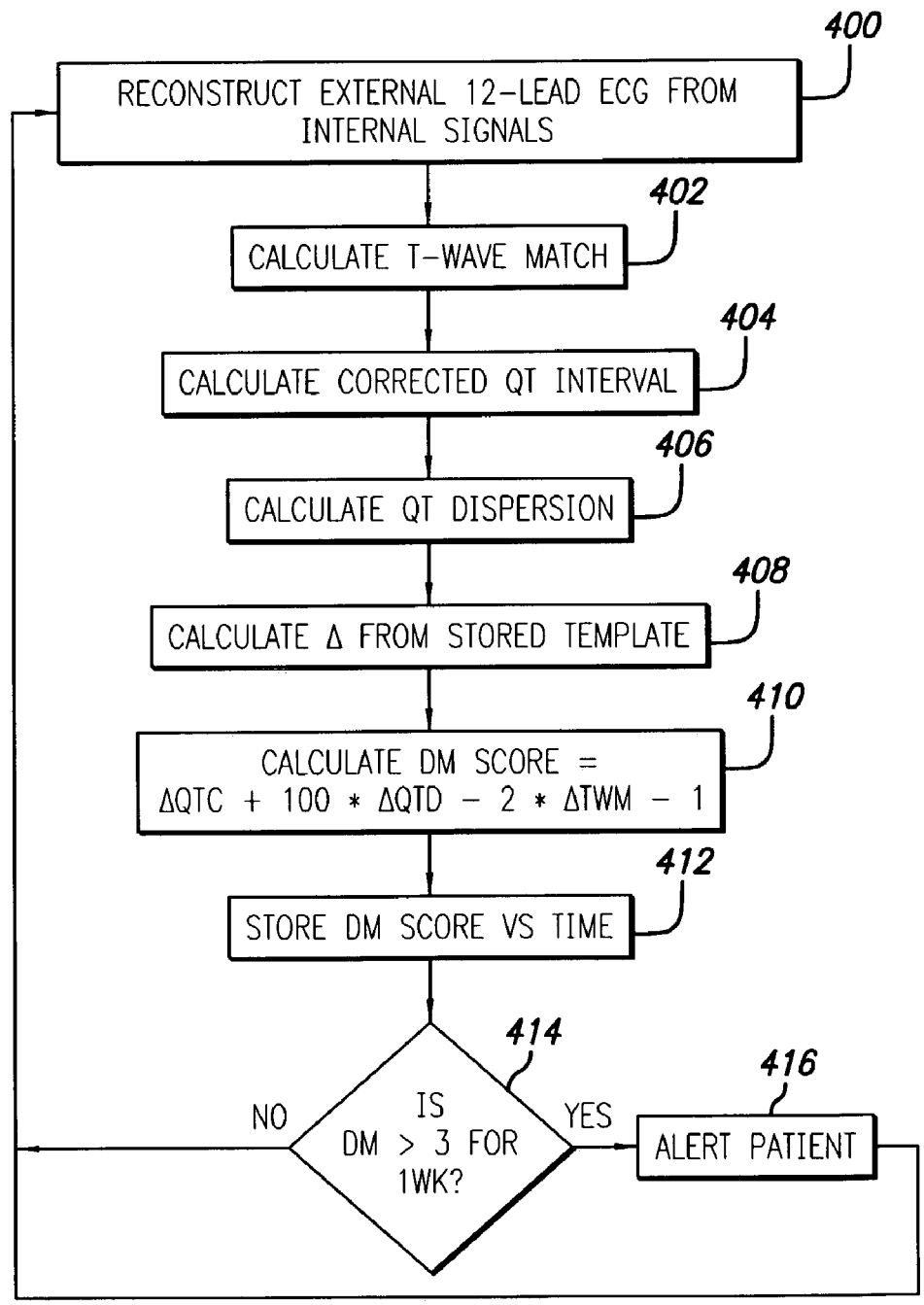
FIG. 4 is a flow chart describing an overview of operation of a preferred embodiment of FIG. 1 in continuous usage in the field.

FIG. 4 is a flow diagram illustrating the preferred steps by which the device 10 detects asymptomatic diabetes in a patient. The process of FIG. 4 begins at block 400 with the reconstruction of the 12 lead external electrogram from the internal cardiac signals. After reconstructing the external electrogram, the process moves to activity block 402 wherein the T-wave morphology value is measured. Next, the process advances to activity block 404 wherein the corrected QT interval is measured. As used herein, a "corrected QT interval" refers to the QT interval corrected for changes in heart rate. For example, the QT interval will be shorter at higher heart rates associated with, for example, exercise, and longer at lower heart rates associated with, for example, rest. The corrected QT interval is based on the RR interval, which is based on the heart rate. The heart rate may be determined directly by measurement, or if paced, indirectly by measuring a level of activity through an activity sensor. After measurement and calculation of the corrected QT interval value, the process moves to activity block 406 wherein the program measures and calculates the QT dispersion value. As used herein, the term "QT dispersion" refers to the difference between the shortest QT interval and the longest QT interval of all leads at a particular point in time. In another embodiment, the microcontroller 60 is programmed to measure and calculate a signal averaged QRS width value, which alone or in combination with other heartbeat characteristics, may be indicative of asymptomatic diabetes.

As the process moves to activity block 408, delta values are calculated. As used herein, "delta values" refer to the differences between the measured values obtained in the steps of FIG. 4 and the reference values obtained during the calibration process as outlined in FIG. 3. Specifically, the microcontroller 60 is programmed at activity block 408 to calculate the following delta values: a T-wave morphology delta value, which is the difference between the measured T-wave morphology value 402 at a fixed time and the reference T-wave morphology value 304 stored in memory 94 at activity block 310; a corrected QT interval delta value, which is the difference between the measured QT interval value 404 and the reference QT interval value 306 stored in memory 94 at activity block 310; and a QT dispersion delta value, which is the difference between the measured QT dispersion value 406 and the reference QT dispersion value 308 stored in memory 94 at activity block 310. The delta values subsequently may be used to determine a diabetes mellitus ("DM") indicator score at activity block 410 according to the following formula:

$$(50 \times \text{corrected QT interval delta value}) + (100 \times \text{QT dispersion delta value}) - (2 \times \text{T-wave morphology delta value}) - 1.0$$

In embodiments that measure a signal averaged QRS width value as an indicator of asymptomatic diabetes, a delta signal averaged QRS width value may be calculated, which value is the difference between the measured signal averaged QRS width value at a fixed time and a reference signal averaged QRS width value stored in memory 94 of the device 10.

As the process reaches activity block 412, the DM indicator score is stored versus time in memory 94. The formula for calculating the DM indicator score is designed such that a value of approximately 0 is returned for healthy patients, while a score between about 2 and about 6 is returned for diabetic patients. After storing the DM indicator score, the process advances to decision block 414 wherein the processor evaluates whether the DM indicator score is greater than a threshold value of 3 for a time period exceeding one week. If the DM indicator score is greater than a value of 3 for a time period exceeding one week, the process advances to activity block 416 and issues an alert to the patient and the system returns to normal monitoring by returning to activity block 400. Conversely, if the DM indicator score is not greater than a value of 3 for a time period exceeding one week, then the process stores the DM indicator score versus time and returns to activity block 400 for normal monitoring. The stored DM indicator score versus time at activity block 412 may be stored for retrieval at a later date by a physician during the patient's follow-up visit.

The coefficients for the DM indicator score algorithm described in FIG. 4 were generally derived from and supported by published literature. For example, it has been demonstrated that abnormal T-wave morphology is associated with diabetes. Accordingly, in deriving a coefficient for the T-wave morphology variable in the DM indicator score, it was determined that an exact match (i.e., a match of 100% identity) between the measured T-wave morphology value 402 and the reference T-wave morphology value 304 would have a value of 1.0. Accordingly, measured T-wave morphology values 402 that are flattened due to hyperglycemia will have an imprecise match (i.e., a match of less than 100% identity) to the template T-wave morphology value 304 and are assigned values lower than 1.0, thereby indicating a negative coefficient. Measured T-wave morphology delta values and risk for diabetes are inversely related. Thus, as the measured T-wave morphology values decrease, the risk for diabetes increases. Matches of about 50% between the measured T-wave morphology value 402 and the reference T-wave morphology value 304 were considered important in the derivation of the DM indicator score; thus, the coefficient for the T-wave morphology delta value was set at 2.

A difference in corrected QT intervals of 0.021 or less seconds between normal and diabetic patients has been reported. Accordingly, to yield an impact value of 1.0 in the DM indicator score algorithm, 50 was selected as the coefficient for corrected QT interval because 50 is approximately the reciprocal of 0.021. Similarly, a difference of 0.009 seconds in QT dispersion between normal and diabetic patients has been reported. Accordingly, to yield an impact value of 1.0 in the DM indicator score algorithm, 100 was selected as the coefficient for QT dispersion because 100 is approximately the reciprocal of 0.009.

One of ordinary skill in the art will appreciate that the preferred algorithm disclosed in FIG. 3 is not the only algorithm that may be employed in calculating a DM indicator score, and a skilled artisan may alter the coefficients to arrive at a different DM indicator score algorithm, which, nonetheless will serve the same function as the DM indicator score in the present invention, i.e., a reference point to be used for detecting abnormal heartbeat characteristics indicative of asymptomatic diabetes in a patient.

Similarly, the threshold value and pre-determined period of time for which the system recognizes whether the threshold value has been exceeded before alerting the patient is a matter of design choice that may be selected by the physician. For example, the system may be programmed to alert the patient if the DM indicator score exceeds a value of 6 for longer than two days. Accordingly, the DM indicator score is not limited to the algorithm disclosed and the invention is meant to encompass other algorithms that measure the relationship between abnormal heartbeat characteristics and asymptomatic diabetes.

Additionally, it is to be understood that while the Figures depict the present invention in terms of preferred embodiments, the present invention may be practiced by measuring fewer than all the isolated characteristics shown in the Figures, any combination of the isolated characteristics shown in the Figures, or by measuring other heartbeat characteristics, such as, for example, signal averaged QRS width, abnormalities of which have been shown to be associated with asymptomatic diabetes.

For example, the microcontroller 60 may be programmed to measure the T-wave morphology either directly from internal cardiac signals or after reconstruction of an external electrogram based on the internal cardiac signals. Similarly, the microcontroller 60 may be programmed to measure the corrected QT interval and/or QT dispersion either directly from internal cardiac signals or after reconstruction of an external electrogram based on the internal cardiac signals. In a situation wherein the microcontroller 60 is programmed to determine asymptomatic diabetes based solely on the isolated and measured characteristic of T-wave morphology, whether it be directly from internal cardiac signals, or after reconstruction of an external electrogram, a measured T-wave morphology value is obtained and used to calculate a delta T-wave morphology value, which may be indicative of asymptomatic diabetes. Specifically, abnormal T-wave morphology has been shown to be associated with diabetes. It is well known that there is a link between flat or inverted T-wave morphology and coronary heart disease. Moreover, it has been shown that inverted T-wave morphology is associated with hyperglycemic patients otherwise not known to manifest either diabetes or heart disease. Additionally, it has been shown that the amplitude of T-waves decreases as the concentration of blood glucose decreases. Furthermore, as shown in FIGS. 5A and 5B, T-wave oversensing has been observed in a patient having an implantable cardiac device. Accordingly, relative changes in T-wave morphology over time, measured either independently or in conjunction with other heartbeat characteristics, may be used to detect asymptomatic diabetics.

Abnormal corrected QT intervals have been shown to be associated with asymptomatic diabetes. Specifically, electrograms from diabetics typically reflect a faster heart rate, a leftward mean frontal QRS axis, a prolonged corrected QT interval and the presence of ST-T waves. Accordingly, relative changes in corrected QT interval over time may be used to detect asymptomatic diabetes. The relative changes may be measured independently or in conjunction with other heartbeat characteristics to detect asymptomatic diabetes in a patient.

QT dispersion is increased in diabetics, suggesting that QT dispersion may be a risk factor for the occurrence of sudden death and cardiac rhythmic disturbances observed in diabetic patients, as well as patients afflicted with coronary heart disease or chronic heart failure. Accordingly, relative changes in QT dispersion over time, measured either independently or in conjunction with other heartbeat characteristics, may be used to identify asymptomatic diabetes.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described.

What is claimed is:

1. In an implantable cardiac stimulation device, a system for detecting asymptomatic diabetes in a patient, the system comprising:
a pulse generator that generates pacing pulses for delivery to a heart;
a sensing circuit that senses internal cardiac signals of the heart;
circuitry connected to the pulse generator and the sensing circuit that is operative to measure at least one characteristic of the internal cardiac signals to provide measured values, and wherein the circuitry is further operative to process the measured values to determine whether the patient has asymptomatic diabetes; and
a memory circuit connected to the circuitry and that is operative to store the measured values.

2. The system of claim 1, wherein the circuitry is further operative to construct a surrogate for an external electrogram based on the internal cardiac signals.

3. The system of claim 2, wherein the surrogate for the external electrogram is a surrogate for a 12 lead electrogram.

4. The system of claim 1, further comprising a calibration circuit operative to calibrate the system and to calculate reference values.

5. The system of claim 1, wherein the sensing circuit senses the internal cardiac signals by far-field electrocardiography.

6. The system of claim 1, wherein the cardiac stimulation device further comprises pacing and sensing leads oriented in parallel to approximate far-field electrocardiography.

7. The system of claim 1, wherein the at least one characteristic of the internal cardiac signals measured to determine whether the patient has asymptomatic diabetes is T-wave morphology.

8. The system of claim 7, wherein the circuitry is programmed to measure a T-wave morphology value, to calculate a delta T-wave morphology value by determining a difference between the measured T-wave morphology value and a reference T-wave morphology value, and to store the delta T-wave morphology values over time, wherein relative changes in the delta T-wave morphology values over time indicate that the patient has asymptomatic diabetes.

9. The system of claim 1, wherein the at least one characteristic of the internal cardiac signals measured to determine whether the patient has asymptomatic diabetes is corrected QT interval.

10. The system of claim 9, wherein the circuitry is programmed to measure a corrected QT interval value, to calculate a delta corrected QT interval value by determining a difference between the measured corrected QT interval value and a reference corrected QT interval value, and to store the delta corrected QT interval values over time, wherein relative changes in the delta corrected QT interval values over time indicate that the patient has asymptomatic diabetes.

11. The system of claim 1, wherein the at least one characteristic of the internal cardiac signals measured to determine whether the patient has asymptomatic diabetes is QT dispersion.

12. The system of claim 11, wherein the circuitry is programmed to measure a QT dispersion value, to calculate a delta QT dispersion value by determining a difference between the measured QT dispersion value and a reference QT dispersion value, and to store the delta QT dispersion values over time, wherein relative changes in the delta QT dispersion values over time indicate that the patient has asymptomatic diabetes.

13. The system of claim 1, wherein the at least one characteristic of the internal cardiac signals measured to determine whether the patient has asymptomatic diabetes is signal averaged QRS width.

14. The system of claim 1, wherein the circuitry is programmed to measure a signal averaged QRS width value, to calculate a delta signal averaged QRS width value by determining a difference between the measured signal averaged QRS width value and a reference signal averaged QRS width value, and store the delta signal averaged QRS width values over time, wherein relative changes in the delta signal averaged QRS width values over time indicate that the patient has asymptomatic diabetes.

15. The system of claim 1, wherein the at least one characteristic of the internal cardiac signals measured to determine whether the patient has asymptomatic diabetes comprises at least one of T-wave morphology and corrected QT interval.

16. The system of claim 15, wherein the circuitry is programmed to measure a T-wave morphology value, to measure a corrected QT interval value, to calculate a delta T-wave morphology value by determining a difference between the measured T-wave morphology value and a reference T-wave morphology value, to calculate a delta corrected QT interval value by determining a difference between the measured corrected QT interval and a reference corrected QT interval value, to store the delta T-wave morphology values over time, and to store the delta corrected QT interval values over time, wherein relative changes in the delta T-wave morphology values and delta corrected QT interval values over time indicate that the patient has asymptomatic diabetes.

17. The system of claim 1, wherein the at least one characteristic of the internal cardiac signals measured to determine whether the patient has asymptomatic diabetes comprises at least one of corrected QT interval and QT dispersion.

18. The system of claim 17, wherein the circuitry is programmed to measure a corrected QT interval value, to measure a QT dispersion value, to calculate a delta corrected QT interval value by determining a difference between the measured corrected QT interval value and a reference corrected QT interval value, to calculate a delta QT dispersion value by determining a difference between the measured QT dispersion value and a reference QT dispersion value, to store the delta corrected QT interval values over time, and to store the delta QT dispersion values over time, wherein relative changes in the delta corrected QT interval values and delta QT dispersion values over time indicate that the patient has asymptomatic diabetes.

19. The system of claim 1, wherein the at least one characteristic of the internal cardiac signals measured to determine whether the patient has asymptomatic diabetes comprises at least one of T-wave morphology, corrected QT interval and QT dispersion.

20. The system of claim 19, wherein the circuitry is programmed to measure a T-wave morphology value, to measure a corrected QT interval value, to measure a QT dispersion value, to calculate a delta T-wave morphology value by determining a difference between the measured T-wave morphology value and a reference T-wave morphology value, to calculate a delta corrected QT interval value by determining a difference between the measured corrected QT interval value and a reference corrected QT interval value, to calculate a delta QT dispersion value by determining a difference between the measured QT dispersion value and a reference QT dispersion value, to store the delta T-wave morphology value over time, to store the delta corrected QT interval value over time, and store the delta QT dispersion value over time, wherein relative changes in the delta T-wave morphology values, delta corrected QT interval and delta QT dispersion over time indicate that the patient has asymptomatic diabetes.

21. The system of claim 1, wherein the circuitry is further operative to calculate a diabetes mellitus indicator score.

22. The system of claim 21, wherein the diabetes mellitus indicator score is stored in a memory over time.

23. The system of claim 22, wherein the circuitry is further operative to compare the diabetes mellitus indicator score to a threshold value stored in the memory, and wherein the system is further operative to alert the patient if the diabetes mellitus indicator score is greater than or equal to the threshold value for a pre-determined period of time.

24. In an implantable cardiac stimulation device, a method for detecting asymptomatic diabetes in a patient, the method comprising:

sensing cardiac signals of the patient's heart using the implantable cardiac stimulation device;

measuring at least one characteristic of the cardiac signals to provide measured values; and analyzing the measured values to determine whether the patient has asymptomatic diabetes.

25. The method of claim 24, wherein sensing cardiac signals comprises sensing the cardiac signals by far-field electrocardiography.

26. The method of claim 24, wherein analyzing the measured values comprises:
   (a) measuring a T-wave morphology value;
   (b) calculating a delta T-wave morphology value by determining a difference between the measured T-wave morphology value and a reference T-wave morphology value, the reference T-wave morphology value determined as a result of a calibration step; and
   (c) storing the delta T-wave morphology value in a memory,
   wherein relative changes in the delta T-wave morphology value over time indicate that the patient has asymptomatic diabetes.

27. The method of claim 24, wherein analyzing the measured values comprises:
   (a) measuring a corrected QT interval value;
   (b) calculating a delta corrected QT interval value by determining a difference between the measured corrected QT interval value and a reference corrected QT interval value, the reference corrected QT interval value determined as a result of a calibration step; and
   (c) storing the delta corrected QT interval value in a memory,
   wherein relative changes in the delta corrected QT interval value over time indicate that the patient has asymptomatic diabetes.

28. The method of claim 24, further comprising calibrating the implantable device prior to detecting asymptomatic diabetes in the patient.

29. In an implantable cardiac stimulation device, a system for detecting asymptomatic diabetes in a patient, the system comprising:
   means for sensing cardiac signals of the heart;
   means for measuring at least one characteristic of the cardiac signals to provide measured values; and
   means for processing the measured values to determine whether the patient has asymptomatic diabetes.

30. The system of claim 29 wherein the means for measuring comprises means for measuring T-wave morphology.

31. The system of claim 29 wherein the means for measuring comprises means for measuring a corrected QT interval.

32. The system of claim 29 wherein the means for measuring comprises means for measuring a signal averaged QRS width.

33. The system of claim 29 wherein the means for measuring comprises means for measuring QT dispersion.

* * * * *